(12) United States Patent  
Haider

(10) Patent No.: US 6,485,494 B1  
(45) Date of Patent: *Nov. 26, 2002

(54) PEDICLE SCREW SYSTEM FOR OSTEOSYNTHESIS

(76) Inventor: Thomas T. Haider, 2357 Knob Hill Dr., Riverside, CA (US) 92506

( * ) Notice: Subject to any disclaimer, the term of this patent is extended or adjusted under 35 U.S.C. 154(b) by 0 days.

This patent is subject to a terminal disclaimer.

(21) Appl. No.: 09/582,826
(22) PCT Filed: Dec. 20, 1996
(86) PCT No.: PCT/US97/23851
§ 371 (c)(1),
(2), (4) Date: Jun. 18, 1999
(87) PCT Pub. No.: WO98/27884
PCT Pub. Date: Jul. 2, 1998

Related U.S. Application Data

(63) Continuation-in-part of application No. 08/771,133, filed on Dec. 20, 1996, now Pat. No. 5,782,833.

(51) Int. Cl.[7] .................................................. A61B 17/58
(52) U.S. Cl. ................................................... 606/73
(58) Field of Search ............................... 606/73, 72, 60

(56) References Cited

U.S. PATENT DOCUMENTS 5,385,583 A * 1/1995 Cotrel .......................... 623/17
6,280,442 B1 * 2/2001 Barker et al. .................. 606/60

* cited by examiner

Primary Examiner—Nicholas D. Lucchesi
Assistant Examiner—Melba Bumgarner
(74) Attorney, Agent, or Firm—Harold L. Jackson

(57) ABSTRACT

The invention is a pedicle screw assembly (10) for use with a rod (11) for the immobilization of bone segments. The assembly is composed of a screw (12), a poly-axial housing (20), a washer (34), a set screw (48), and a cup shaped washer (40). When the screw is placed inside the poly-axial housing (21), the head of the screw (12) comes into contact with a middle section of the poly-axial housing (18), and is secured into the bone so that the poly-axial housing is pivotable. The housing includes a pair of upstanding posts (38) with interior threads. A washer (24) is inserted between the head of the screw (12) and the rod. A cap (40), having a bottom with a pair of openings (43) and a lateral cross connector (44), is placed over the posts (38) so that the cross connector (44) engages the rod. The cross connector and washer have semi-cylindrical rod engaging surfaces. A set screw (42) is threaded into the housing posts to secure the rod.

20 Claims, 4 Drawing Sheets

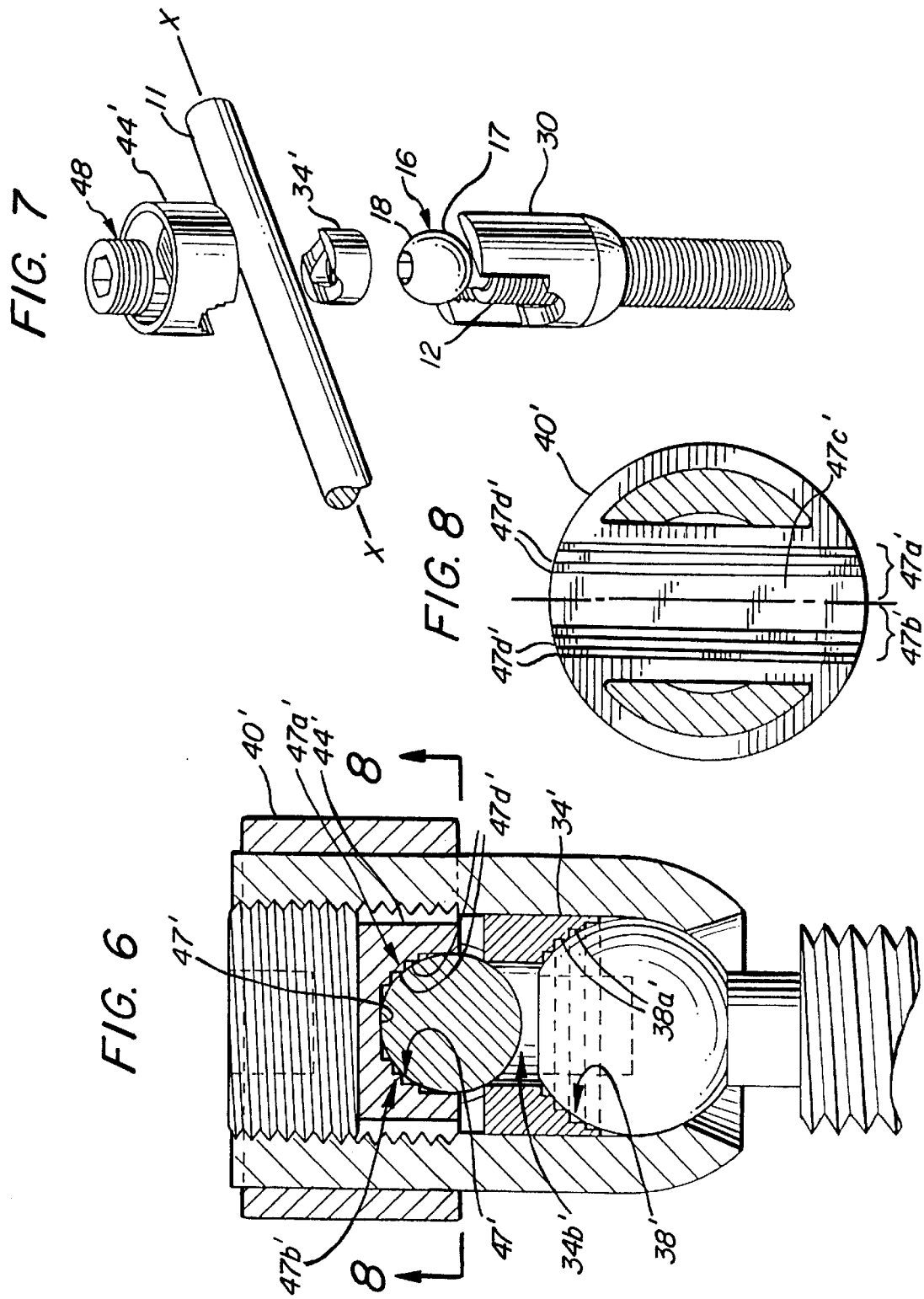

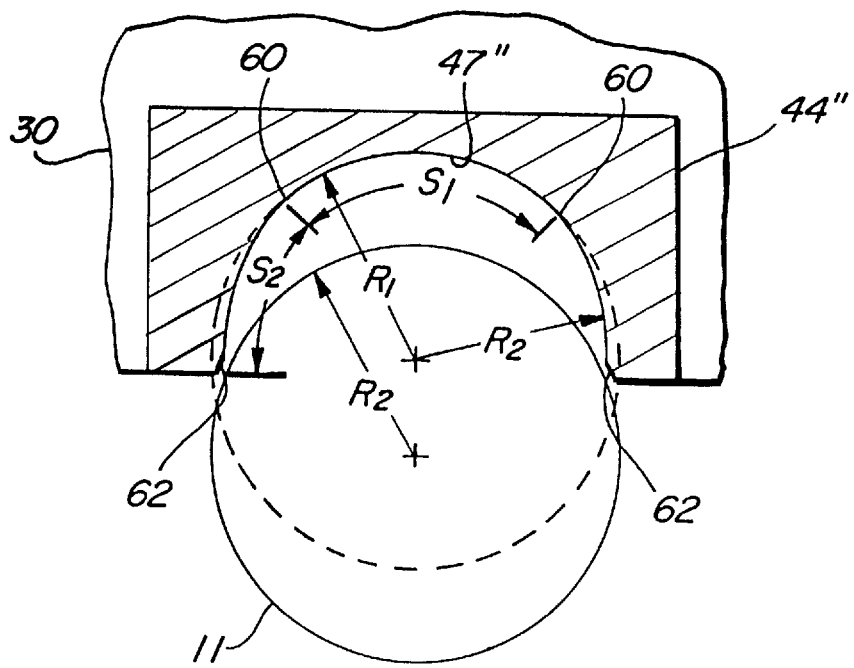
FIG. 9
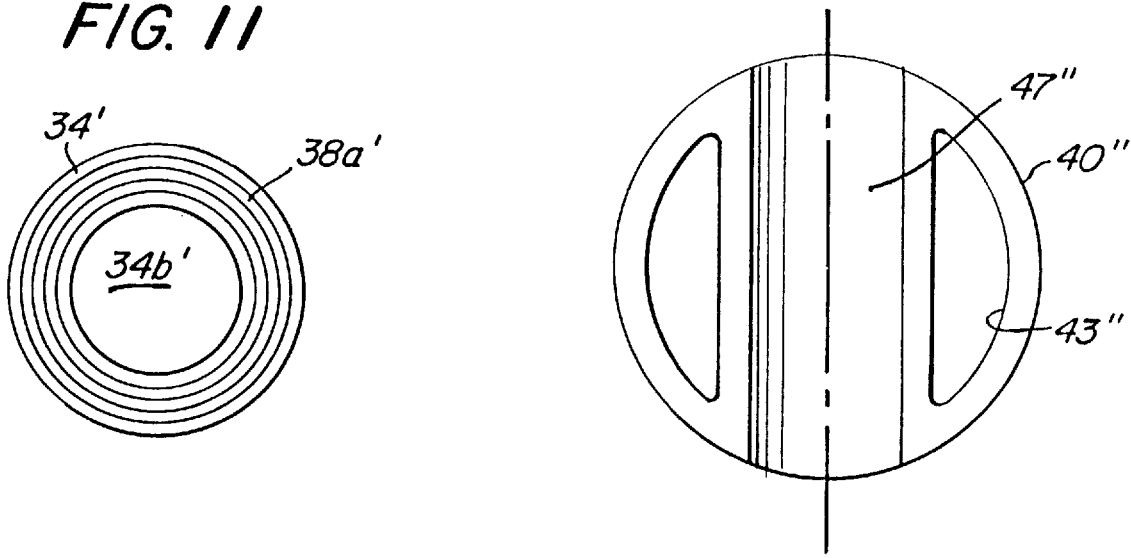
FIG. 10
FIG. 11

PEDICLE SCREW SYSTEM FOR OSTEOSYNTHESIS

RELATED APPLICATION

This application is a continuation-in-part of my application Ser. No. 08/771,133 filed Dec. 20, 1996 entitled Pedicle Screw System for Osteosynthesis, now issued U.S. Pat. No. 5,782,833 and further claims priority of PCT/US97/23851 filed Dec. 19, 1997.

TECHNICAL FIELD

The present invention relates to the medical field commonly referred to as Osteosynthesis, i.e., the fusion between segments of the spine and more particularly to a pedicle screw and rod system for immobilizing the segments during the fusion process.

BACKGROUND ART

Osteosynthesis is achieved by immobilizing the bone. When trying to achieve osteosynthesis and specifically fusion between different segments of the spine, one has to provide some type of immobilization. There are various prior art systems which try to achieve this purpose. The different systems involve placement of screws into the bone. The screws are then connected to each other by use of various sizes of rods or a plate. The bone segments that are being connected, especially in the spine, may be carrying different angles and different medical-lateral positions. Placement of a rod with a rigid screw or placement of a plate between two rigid screws is difficult because of the medial lateral displacement or angulation at different segments. One has to bend the rod or plate and at times achieve a complex bend in order to connect two different segments of the bone and especially two different areas in the spine. When dealing with the spine, the screws are ordinarily placed into the Pedicle, and due to the different positions of the pedicle and different angulations of the screw as it enters the pedicle, one encounters difficulty in positioning and connecting these screws at various points.

Even though one can create a complex bend at the rod or the plate in order to connect two or more screws, there are places in the pedicle where one runs the chance of stress risers at different points and breakage of the system as the bends can never be perfect.

A screw system, which is capable of accommodating the rod in a perfect location without creating any appreciable areas of stress riser, will alleviate some of the above problems. Such a screw system would allow the rod to be bent to achieve fixation between two different points while adjusting to any imperfections in the bend.

There is at least one polyaxial screw system that has been used in the past which will achieve some of these goals; however, there are some inherent problems with this particular system. This polyaxial screw has many components which makes placement of such a screw cumbersome, which in turn, lengthens the operative time for this particular procedure. The system has a locking screw on the inside as well as a locking nut on the outside of the housing, which causes the operation to take much longer to perform. The fixation point which will lock the polyaxial screw and keep it from angling once the system is tightened is also not ideal.

Several patents teach the use of a pedicle screw system which appear to provide several degrees of freedom (i.e., rotation and limited angular deflection about a fixed point) for the immobilization of bone segments. See for example U.S. Pat. No. 5,360,431 to Puno et al, U.S. Pat. No. 5,443,467 to Biedermann et al and U.S. Pat. No. 5,176,678 to Tsou. Each of these patented structures has certain drawbacks including the use of a conventional nut to secure the rod into place for support of the bone segments. The nuts have flat surrounding edges which are engaged by a wrench to tighten the nut. Due to the surrounding tissue, and the confined area, difficulty can arise in placing the nut in the correct position thus requiring even more time to perform the operation. During the operation the patient is under anesthesia and this extra time increases the risk to the patient. Also, when secured the nut protrudes into the surrounding soft tissue after the operation is completed. This protrusion can lead to irritation of the surrounding soft tissue and possibly inflammation.

Another problem arising with the use of the nut is the tightening process. The nut is secured through the use of a wrench. The wrench requires space around the nut to be operable which necessarily increases the scope of the surgical procedure. Furthermore, the wrench should not come into contact with the surrounding soft tissue to avoid the possibility of peripheral tissue damage. These limitations tend to further increase the risk to the patient during the operation.

Yet another problem with the prior art systems involves the manner in which the screw system is affixed to the rod. For example, systems like that disclosed in the Biedermann et al patent utilize washers or nuts on each side of the rod to secure the rod to the housing. The nuts or washers have planar surfaces which make contact with the rod only along segments of a line. Such a minimal contact with the rod will not provide sufficient purchase on the surface of the rod to prevent post operative movement between the rod and housing. Unless the screw housing is firmly grasps the rod the rod will have a tendency to twist or rotate inside of one or more of the housings. If the rod is allowed to rotate relative to one housing (and associated screw) while an adjacent housing and screw remain locked to the rod the screw secured to the locked housing may travel and break out of the vertebrae in which it was embedded. This will result in a damaged vertebrae and perhaps a severed nerve exiting the spinal column at that point. If the rod is allowed to rotate relative to all of the several housings to which it was originally secured it may migrate into muscle, soft tissue or even into the spinal column itself.

There is a need for a more reliable pedicle screw and rod system which may readily and rapidly be secured in place, with less bulky equipment and which is less intrusive to the surrounding soft tissue.

SUMMARY OF THE INVENTION

The present invention addresses the stabilization of bone segments through the use of a polyaxial pedicle screw assembly and rod. The rod is arranged to be secured between two or more embedded screw assemblies to immobilize segments of the spine. The assembly includes a screw which has a head and a threaded cylindrical shaft and is threaded into the bone. The head of the screw has a top and bottom, both of which are spherically convex in shape with the head being larger than the diameter of the cylindrical shaft. The top of the screw head has a wrench engaging surface, such as an allen wrench socket.

The screw fits within a polyaxial housing having a stepped bore adapted to receive the rod. The polyaxial housing is divided into three sections. The top section of the housing receives the entire screw including the head and is formed by a pair of spaced upstanding posts which define a U-shaped slot therebetween for receiving the rod. The inner walls of the posts are threaded for receiving a set screw which secures the rod in place. The middle section of the housing has an inner spherically concave surface for cradling the bottom of the head of the screw. The bore through the bottom section has a diameter which allows only the threaded cylindrical shaft to pass through. The screw, after insertion into the polyaxial housing, is threadably secured into the bone.

A washer with a generally spherically concave bottom surface to engage the head of the screw is then placed within the housing. Preferably the bottom surface of the washer is provided with a roughened surface, such as asperities in the form of sharp edges to provide a locking action between the washer and the screw head in the assembled condition. The top of the washer is provided with a concave surface, preferably semicylindrical or saddle shaped, to conform to the shape of the rod.

The lower surface of the washer provides for a positive gripping surface area with the screw head thereby adding to the stability of the rod and screw, once in place.

The screw assembly further includes a cup-shaped cap having two opposing openings to receive the posts and a cross-connector extending across the bottom of the cap. The cross-connector has a flat top and a bottom with a concave semicylindrical or longitudinal saddle shape to conform to the shape of the rod. The cup-shaped cap is adapted to be placed over the polyaxial housing with the bottom surface of the cross-connector making contact with the rod.

A set screw of conventional configuration is arranged to be threaded into the top section of the polyaxial housing by means of a wrench inserted into a wrench engaging surface, such as a allen wrench socket, in the top of the set screw, to tighten the assembly into place. The rod engaging surface of the cross connector may be provided with asperities formed, for example, by a series of sharp ridges (or edges) running parallel to the longitudinal axis of the rod or formed with a smaller radius of curvature at the bottom than at the top so that the cross connector will firmly grasp the rod and prevent it from twisting within the housing when the set screw is tightened.

With the set screw in place, but not tightened, the assembly has three degrees of freedom, i.e., rotatable and angularly positionable about the head of the screw. The tightening of the set screw secures the assembly into a single position. The set screw allows the assembly to be tightened while overcoming the disadvantage of potential soft tissue damage due to the use of a nut. The screw assembly of the present invention when secured in place does not protrude into the surrounding soft tissue and thus reduces the risk of irritation and soft tissue damage.

The present invention provides a highly flexible and stable bone segment immobilization system with a minimum number of components which results in a reduction in the time that a patient must remain under anesthesia.

The construction and operational features of the present invention may best be understood by reference to the following description taken in conjunction with the appended drawings in which like components in the several figures are identified by the same reference numerals.

BRIEF DESCRIPTION OF THE DRAWINGS

FIG. 6 is a cross-sectional view of an alternative embodiment of the assembly showing only a portion of the screw shaft;

FIG. 7 is an exploded view of the assembly of FIG. 6;

FIG. 8 is a cross-sectional view of the assembly taken along lines 8—8 of FIG. 6;

FIG. 9 is a partial cross sectional view showing an alternative design for the rod engaging surface of the cap cross connector;

FIG. 10 is a bottom plan view of the alternative cap arrangement shown in FIG. 9; and FIG. 11 is a bottom plan view of the washer utilized in the embodiment of FIG. 6.

DESCRIPTION OF THE PREFERRED EMBODIMENT

Figure 1:
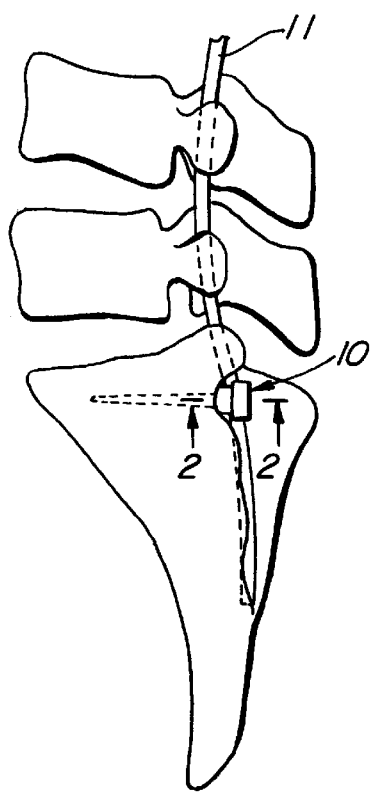
FIG. 1 is a diagrammatic view of several segments of a spiral column with a pedicle screw assembly and rod, in accordance with the present invention, secured thereto.

Referring now to the drawings and particularly to FIG. 1, a pedicle screw assembly 10, in accordance with the present invention, is intended to be secured in bone segments of a patient's spine and in conjunction with a rigid (though bendable) rod 11, to immobilize and allow the segments to fuse together.

Figure 2:
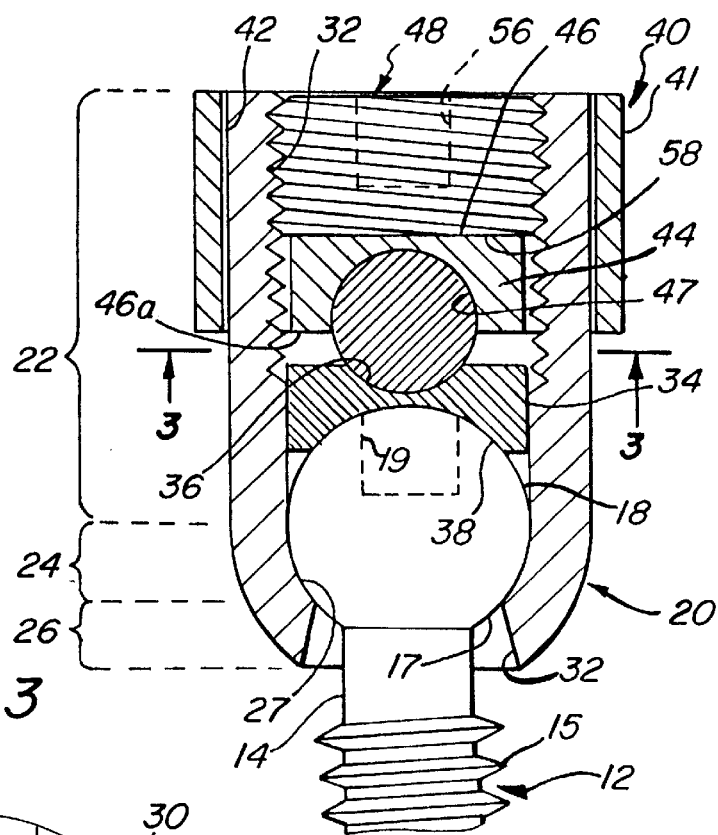
FIG. 2, is a cross-sectional view of the assembled pedicle screw assembly taken along lines 1—1 of FIG. 1, showing only a portion of the screw shaft.
Figure 3:
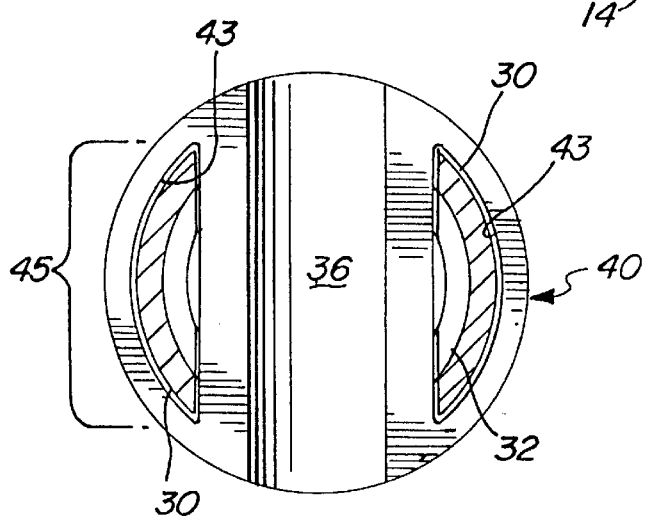
FIG. 3 is a cross-sectional view of the assembly taken along lines 3—3 of FIG. 2, showing the top of the washer, the housing posts and the lower end of the cap, but not the rod.
Figure 4:
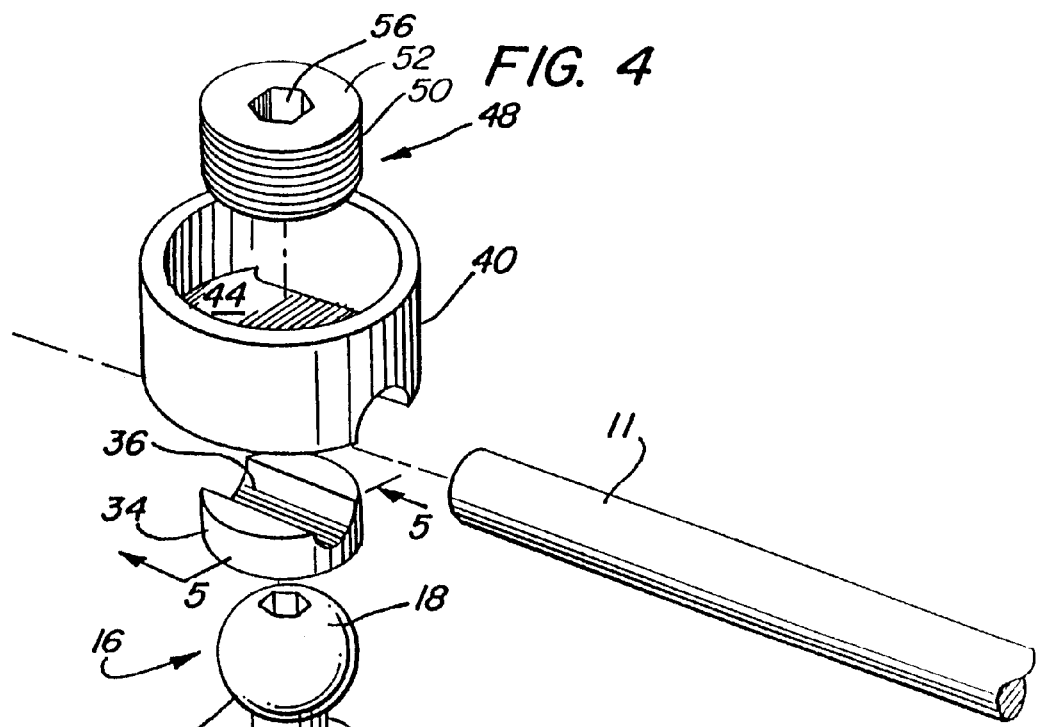
FIG. 4 is an exploded view of the screw assembly and rod.

As is illustrated in FIGS. 2 and 4, the screw assembly 10 includes a pedicle screw 12 which has a cylindrical shaft 14 threaded at 15, and a head 16 formed integrally with the shaft. The head of the screw is spherical, except for the junction of the shaft with the head. The spherical surface of the head of the screw is divided into upper and lower surfaces with each surface (i.e., lower 17 and upper 18) being generally semispherical. The top of the head of the screw includes an indentation in the form of a wrench engaging surface 19. The wrench engaging surface 19 is illustrated in the form of a hexagonal socket for receiving a suitable wrench such as an allen wrench. The wrench engaging surface could also be in the form of a slot for receiving a screwdriver or any other suitable recessed shape. The head of the screw has a diameter which is larger than the diameter of the threaded shaft 14 as is illustrated in FIG. 2.

A polyaxial housing 20 for receiving the screw, is composed of a top 22, a middle 24 and bottom section 26, as shown in FIG. 2. A stepped axial bore 28 extends through the housing with the bore in the top section 22 having a diameter larger than the diameter of the threaded shaft of the screw. The top section defines a pair of upstanding posts 30 with a rod receiving slot 31 therebetween. The inside walls 32 of the posts are threaded to receive a set screw, to be described. The middle section 24 of the housing defines an inner generally spherically concave surface 27 adapted to engage the convex semi-spherical bottom surface 17 of the head of the screw.

The bore in the bottom section 26 of the housing has a diameter which is greater than the diameter of the threaded cylindrical shaft 14, but smaller than the diameter of the head 16 of the screw. During assembly the screw is placed within the polyaxial housing 20 such that the bottom 17 of the head of the screw 12 comes into contact with the spherically concave portion of the middle section 27, as is illustrated in FIG. 2. The head of the screw is thus captured or retained within the lower portion of the housing 20. The top section 22 of the housing has a cylindrical outer surface 33, interrupted by the slot 31 and the middle and bottom sections have a generally spherical exterior surface 39 which extends from the upper surface 33 to the bore 28.

Figure 5:
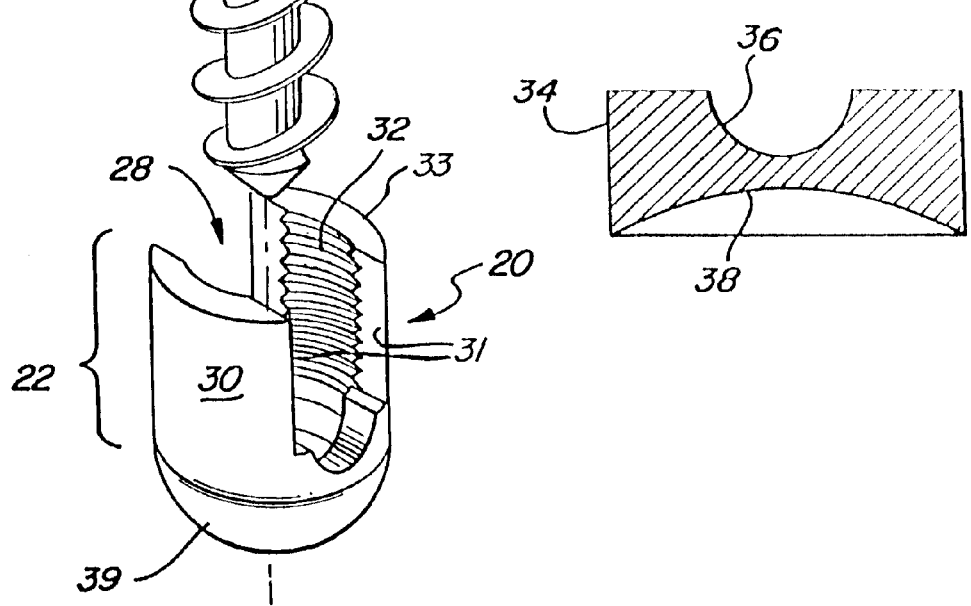
FIG. 5 is a cross-sectional view of the washer taken along lines 5—5 of FIG. 4.

A washer 34 is adapted to be placed between the rod and the upper surface of the head of the screw as is illustrated in FIGS. 2 and 4. The top surface of the washer 34 includes a generally concave semicylindrical rod engaging surface 36 which receives the rod 11. The bottom of the washer has a generally spherically concave screw head engaging surface 38 for engaging the top surface 18 of the head of the screw 12. See FIG. 5.

A cup-shaped cap 40, having a cylindrical outer and inner surface 41 and 42, respectively, is adapted to be placed over the polyaxial housing 20 and engage the top of the rod 11, as is illustrated in FIGS. 2 and 4. The cap 40 has a bottom with a pair of spaced arcuate openings 43 for receiving the posts 30 and a cross-connector 44 spanning the lateral width of the lower inside surface of the cap between the openings. The cross-connector 44 has a top 46 that is flat and a bottom 46a that includes a longitudinal concave rod-engaging surface 47 (i.e., semicylindrical, saddle or U-shaped surface). The cap is adapted to be placed over the outside of the polyaxial housing so that the posts 30 extend through the openings 43 thus allowing the cross-connector to be received between the posts and within the slot 28 of the housing. The cup-shaped cap 40 is arranged to proceed downwardly within the axial bore of the polyaxial housing until the rod engaging surface of the cross-connector comes into contact with the rod 11.

A conventional set screw 48 completes the pedicle screw assembly. The set screw includes external threads 50, a top 52, and a bottom 58. The top 52 has a hexagonal indentation or recess which serves as a wrench engaging surface 56, i.e., a hexagonal socket. The bottom 58 is flat. When inserted into the axial bore of the polyaxial housing the threads of the set screw come into contact with the threads on the inner walls of the posts 30. As the set screw 48 is tightened, the bottom of the set screw 58 comes into contact with the top of the cross-connector 44 forcing the housing upwardly or the rod downwardly or both until the rod is firmly captured between the head of the implanted screw (including the washer) and the cap. The outer segments 45 of the cap 40 serve to support the posts 30 and prevent the posts from moving outwardly or spreading apart when the set screw is tightened thereby insuring a stable assembly.

Since the set screw fits inside of the polyaxial housing, there is no contact between the set screw and the tissue of the patient. This reduces the risk of tissue damage and allows for a more limited area of surgical intrusion for the installation of the pedicle screw assembly. Further, the wrench engaging surface is more accessible and requires a less bulky wrench or securing device to accomplish the tightening process. These factors lessen the time required for the operation, minimize tissue damage, and utilizes a smaller securing device to fix the assembly into position.

Before the final tightening operation, the polyaxial housing is freely rotatable and angularly displaceable about the head of the implanted screw. This freedom of movement, to accommodate any bends in the rod, is referred to herein as three degrees of freedom. As the proper alignment is achieved, the assembly can be secured in a single desired position by the final tightening of the set screw.

As a result of this procedure, the bone segments are brought into a stable immobilized position. This is best understood by referring to FIG. 1. This figure shows the pedicle assembly and rod in place for the immobilization of spinal bone segments. The rod is connected to other pedicle screw assemblies, not shown, and thus keeps the bone segments in an immobilized state.

The components of the screw assembly as well as the rod may be made of a high strength material, such as stainless steel, or preferably titanium, which is compatible with the surrounding bone and tissue.

An alternative cap 40', with a preferred rod engaging surface 47' and an alternative washer design 34' with a preferred screw head engaging surface 38', are illustrated in FIGS. 6–8 and 11. Each of the two sides 47a' and 47b' of the rod engaging surface 47' of the cap cross connector 44' (which straddle an upper center section 47c') are formed in an upwardly extending stair step pattern which results in inwardly protruding sharp ridges 47d'. These sharp ridges extend parallel to the longitudinal axis x—x of the rod and are forced against the rod surface when the set screw is tightened. The sharp ridges inhibit any rotational motion or twisting of the rod.

The washer 34' has a roughened surface formed by stair step pattern of circular sharp edges or ridges 38a' concentrically arranged around the central axis y—y of the housing. The stair step pattern extends upwardly from the bottom of the washer to a central opening 34b'. The sharp edges are forced against the upper surface of the screw head when the set screw is tightened to fix the angular position of the housing relative to the screw.

The biting action of the sharp edges 38' a vis a vis the screw head firmly locks the housing in place relative to the screw head.

Referring now to FIGS. 9 and 10, there is illustrated another alternative design for the rod engaging surface of the cap cross connector 44". The cross connector 44" is formed with a cross sectional radius $R_1$, over a central sector $S_1$, which is substantially the same radius of the rod. Beginning at the ends 60 of the sector $S_1$, the radius is gradually decreased (i.e., over a sector $S_2$) to a radius $R_2$ (slightly smaller than $R_1$) at the bottom 62 of the recess as is illustrated in FIG. 9. The difference in the radii $R_1$ and $R_2$, which need only be a few thousands of an inch, allows the cross connector 44" to snap over the outer surface of the rod 11 with an interface fit and effectively and securely clamps the cap to the rod when the set screw is tightened. This ensures that the rod will not rotate, twist or slide longitudinally within the housing.

The parameters of the present device may be altered in numerous ways without departing from the spirit and scope of the invention as defined in the appended claims. Therefore, it is intended that the drawing be interpreted as illustrative and not in any way viewed as being a limitation on the invention.

I claim:

1. A pedicle screw assembly for use in conjunction with a rod for immobilizing bone segments comprising:
    a screw having a threaded shaft for insertion into a bone segment and an enlarged head;
    a polyaxial housing having an upper and lower portion, the head of the screw being captured in the lower portion of the housing, the housing being free to rotate and pivot relative to the head of the screw and having a pair of upstanding posts forming the upper portion of the housing, the posts defining a U-shaped slot therebetween to accommodate the rod and having interior threads;
    a set screw arranged to be threaded into the interior threads of the housing to clamp the assembly to the rod;
    a cup-shaped cap having two opposing openings which fit over the posts and a cross connector extending across the bottom thereof, the cross connector being positioned within the U-shaped slot, between the set screw and the rod, and defining a concave generally saddle-shaped rod engaging surface for engaging the upper surface of the rod, the rod engaging surface being arranged to clamp against the rod when the set screw is tightened; and a washer positioned within the housing between the rod and the head of the screw, the washer having a concave generally saddle-shaped upper surface for engaging the lower surface of the rod, the lower surface of cross connector and the upper surface of the washer serving to firmly grasp the rod when the set screw is tightened to prevent the rod from rotating or moving longitudinally within the housing.

2. The pedical screw assembly of claim 1 wherein the rod engaging concave surface of the cross connector includes a plurality of sharp projections which tend to bite into the surface of the rod when the set screw is tightened.

3. The pedical screw assembly of claim 2 wherein the rod engaging concave surface of the cross connector is formed with a plurality of sharp ridges extending parallel to the longitudinal axis of the rod.

4. The pedical screw assembly of claim 3 wherein the rod engaging concave surface of the cross connector has opposing sides and wherein each side is formed in an upwardly extending stair step pattern.

5. The pedical screw assembly of claim 2 wherein the rod engaging concave surface of the cross connector forms a recess which is generally semicylindrical in cross section with the bottom of the recess having a radius which is slightly smaller than the radius of the rod, whereby the bottom of the cross connector is forced outwardly to snap over the outer surface of the rod when the set screw is tightened.

6. The pedicle screw assembly of claim 1 wherein the head of the screw has a generally semispherical upper surface and wherein the washer has a generally semispherical lower surface for engaging the upper surface of the head of the screw.

7. The pedicle screw assembly of claim 6 wherein the lower surface of the washer has a roughened surface for grasping the head of the screw and maintaining the housing in a fixed angular relationship to the screw once the set screw is tightened.

8. The pedicle screw assembly of claim 7 wherein the lower surface of the washer is formed with a plurality of sharp protruding edges.

9. The pedicle screw assembly of claim 8 wherein the sharp protruding edges form a circular pattern on the lower surface of the washer.

10. The pedicle screw assembly of claim 9 wherein the washer defines a bottom and wherein the protruding edges define a stair step pattern of concentric circles decreasing in diameter and extending upwardly from the bottom of the washer.

11. A pedicle screw assembly for use in conjunction with a cylindrical rod for immobilizing bone segments comprising:

a screw having a threaded shaft for insertion into a bone segment and an enlarged head with a generally convex semispherical top and bottom surface;

a polyaxial housing, the housing having a generally spherical concave inside surface on the lower portion thereof which contacts the bottom surface of the head of the screw to allow the housing to rotate and pivot relative to the head of the screw the housing including a pair of upstanding posts which form the upper portion of the housing, the posts defining a U-shaped slot therebetween to accommodate the rod and having interior threads;

a set screw arranged to be threaded in to the housing threads to clamp the assembly to the rod;

a cup-shaped cap defining diametrically opposed openings which fit over the posts so that the cap prevents the housing posts from spreading apart when the set screw is tightened, the cap having a cross connector extending across the bottom thereof, the cross connector being positioned within the U-shaped slot, between the set screw and the rod, and defining a concave semicylindrical lower surface for gripping the upper surface of the rod; and a washer positioned within the housing between the rod and the head of the screw, the washer having a concave generally semicylindrical upper surface for gripping the lower surface of the rod, and a generally semispherical lower surface for engaging the upper surface of the head of the screw, the lower surface of the cross connector and the upper surface of the washer serving to firmly grasp the rod therebetween when the set screw is tightened to prevent the rod from rotating or moving longitudinally within the housing, the lower surface of the washer serving to grasp the head of the screw and secure the housing in a fixed position relative to the head of the screw when the set screw is tightened.

12. The pedical screw assembly of claim 11 wherein the rod gripping concave surface of the cross connector includes a plurality of sharp projections which tend to bite into the surface of the rod when the set screw is tightened.

13. The pedical screw assembly of claim 12 wherein the rod gripping concave surface of the cross connector is formed with a plurality of sharp ridges extending parallel to the longitudinal axis of the rod.

14. The pedical screw assembly of claim 13 wherein the rod gripping concave surface of the cross connector has opposing sides and wherein each side is formed in an upwardly extending stair step pattern.

15. The pedical screw assembly of claim 12 wherein the rod gripping concave surface of the cross connector defines a recess with a bottom, the recess extending upwardly from the bottom and having a generally semicylindrical cross section with a radius $R_2$ at the bottom thereof which is slightly smaller than the radius of the rod, whereby the bottom of the cross connector is forced outwardly to snap over the outer surface of the rod when the set screw is tightened.

16. The pedical screw assembly of claim 15 wherein the rod gripping surface of the cross connector is formed with a central sector (51) having a cross-sectional radius $R_1$ substantially equal to the radius $R_1$ of the rod and end sectors (52) extending between the central sector and the bottom of the recess, the cross-sectional radius of the surface decreasing from the ends of the central sector to radius $R_2$ at the bottom of the recess.

17. The pedicle screw assembly of claim 11 wherein the lower surface of the washer has a roughened surface for grasping the head of the screw and maintaining the housing in a fixed angular relationship to the screw once the set screw is tightened.

18. The pedicle screw assembly of claim 17 wherein the lower surface of the washer is formed with a plurality of sharp protruding edges.

19. The pedicle screw assembly of claim 18 wherein the sharp protruding edges form a circular pattern on the lower surface of the washer.

20. The pedicle screw assembly of claim 19 wherein the protruding edges define a stair step pattern of concentric circles decreasing in diameter from the bottom of the washer.

* * * * *

UNITED STATES PATENT AND TRADEMARK OFFICE
CERTIFICATE OF CORRECTION

PATENT NO.     : 6,485,494 B1
DATED          : November 26, 2002
INVENTOR(S)    : Haider It is certified that error appears in the above-identified patent and that said Letters Patent is hereby corrected as shown below:

Column 1,
Line 37, "Pedicle" should read -- pedicle --.

Column 6,
Line 28, "38' a" should read -- 38'a --.

Column 8,
Line 46, "(51)" should read -- $S_1$ --.
Line 48, "(52")" should read -- $S_2$ --.

Signed and Sealed this

Eleventh Day of March, 2003

JAMES E. ROGAN
*Director of the United States Patent and Trademark Office*